United States Patent [19]

Shim

[11] Patent Number: 4,511,481
[45] Date of Patent: Apr. 16, 1985

[54] MULTIFUNCTIONAL ADDITIVES

[75] Inventor: Joosup Shim, Wenonah, N.J.

[73] Assignee: Mobil Oil Corporation, New York, N.Y.

[21] Appl. No.: 528,028

[22] Filed: Aug. 31, 1983

[51] Int. Cl.³ .................. C10M 1/32; C10M 1/44
[52] U.S. Cl. ........................... 252/32.5; 252/49.9; 252/394; 252/401
[58] Field of Search ............... 252/32.5, 49.9, 394, 252/401

[56] References Cited

U.S. PATENT DOCUMENTS

| | | | |
|---|---|---|---|
| 3,979,308 | 9/1976 | Mead et al. | 252/32.5 |
| 3,986,967 | 10/1976 | Okorodudu | 252/49.9 |
| 4,118,329 | 10/1978 | Holten | 252/32.5 |
| 4,144,180 | 3/1979 | Andress, Jr. | 252/32.5 |

*Primary Examiner*—Jacqueline V. Howard
*Attorney, Agent, or Firm*—Alexander J. McKillop; Michael G. Gilman; Howard M. Flournoy

[57] ABSTRACT

Synthesized- and mineral-based industrial lubricants are stabilized with a triazole adduct of amine phosphates thereby providing excellent oxidation stability, antiwear and rust preventative performance for said industrial lubricants.

18 Claims, No Drawings

MULTIFUNCTIONAL ADDITIVES

BACKGROUND OF THE INVENTION

1. Field of the Invention

This application is directed to lubricant additives and compositions thereof. More particularly, this application is directed to circulating/gear oils having antioxidant, antiwear and rust inhibiting properties.

2. Description of Prior Art

Triazoles are known to have been employed in lubricant compositions as metal deactivators, for example, U.S. Pat. No. 3,597,353 discloses the use of 4,5,6,7-tetrahydrobenzoltriazole as metal deactivater for natural and synthetic lubricants.

U.S. Pat. No. 4,060,491 discloses the use of 5-alkyl benzoltriazoles, in which the alkyl group contains from 4-16 carbon atoms, in a method for reducing wear between moving steel on steel surfaces.

U.S. Pat. No. 4,371,447 discloses the use of amine phosphates in micro-emulsions.

U.S. Pat. No. 3,788,993 teaches that benzotriazoles react with alkyl or alkenyl succinic anhydrides to form reaction products which impart corrosion inhibiting properties to lubricating oils.

However, no prior art known to applicant discloses and claims lubricant compositions comprising tolyl triazole adducts of amine phosphates as highly effective multifunctional additives as in the present invention.

SUMMARY OF THE INVENTION

It has now been found that adducts of tolyl triazole compounds and amine phosphates impart excellent oxidation stability, antiwear and rust preventive performance to lubricant compositions to which they are added. They are particularly effective with respect to both synthesized and mineral based industrial lubricants. In general, the adducts of the present invention are formed by reacting tolyl triazole (TTZ) with an aromatic amine phosphate.

The triazole compound used to form the adducts of the present invention has the general formula

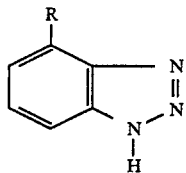

where R is lower alkyl, $C_1$ to about $C_6$, preferred is $R=CH_3$. However, other triazoles such as benzotriazole would also be expected to be useful in providing similar type adducts.

The aromatic amine phosphates which may be utilized in preparing adducts of the present invention have the general formula

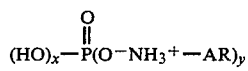

where $x+y=3$ and $Ar=$hydrocarbyl which includes aromatic including aryl and alkaryl.

The adducts of the present invention may be formed by reacting the triazole compound with the aromatic amine in a mole ratio of about 1:3 to about 3:1 of TTZ to amine. Reaction temperatures range from about 80° C. to 125° C. with about 95° C. to about 100° C. being preferred. In general, the reactants are contacted for about 1 to 8 hours with from about 2 to about 4 hours being preferred. The reaction is usually carried out at ambient pressures, however, higher pressures may be used if desired. As those of skill in the art are aware, the particular reaction parameters utilized depend upon the temperature and pressure selected and the specific reactants employed. Thus, at higher temperatures and pressures the reaction time may be shorter than the time at lower temperatures and pressures for a given pair of reactants.

The reaction may proceed with or without the presence of a catalyst. However, a catalyst of an acidic nature, such as acetic acid, propionic acid, toluenesulfonic acid, phosphoric or polyphosphoric and methanesulfonic acids may be effectively employed. Basic catalysts may also be used. Typical examples include sodium or potassium alkoxides, sodium or potassium metal or hydroxides, etc.

Of particular significance in the present invention is the ability of the adducts to improve resistance to oxidation and provide improved anticorrosion characteristics to oleaginous materials such as lubricating media which may comprise liquid oils in the form of either a mineral or a synthetic oil of lubricating viscosity or in the form of a grease in which the aforementioned oils may be employed as a vehicle. In general, mineral oils of paraffinic, naphthenic and mixtures thereof when employed as a lubricant or grease vehicle may be of any suitable lubricating viscosity range. For example, about 45 SSU at 100° F. to about 6000 SSU at 100° F. and preferably from about 50 to about 250 SSU at 200° F. These oils may have viscosity indexes ranging to about 100 or higher. Viscosity indexes from about 70 to about 95 are preferred. The average molecular weights of these oils may range from about 250 to about 800.

Where the lubricant is to be employed in the form of a grease, the lubricating oil is generally employed in an amount sufficient to balance the total grease composition, after accounting for the desired quantity of the thickening agent, and other additive components to be included in the grease formulation. A wide variety of materials may be employed as thickening or gelling agents. These may include any of the conventional metal salts or soaps, which are dispersed in the lubricating vehicle in grease-forming quantities in such degree as to impart to the resulting grease composition the desired consistency. Other thickening agents that may be employed in the grease formulation may comprise the non-soap thickeners, such as surface modified clays and silicas, aryl ureas, calcium complexes and similar materials. In general, grease thickeners are employed which do not melt and dissolve when used at the required temperature within a particular environment; however, in all other respects, any material which is normally employed for thickening or gelling hydrocarbon fluids for forming grease can be used in preparing the improved greases in accordance with the present invention.

In instances where synthetic oils, or synthetic oils employed as the vehicle for the grease, are desired in preference to mineral oils, or in combination therewith, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl)sebacate, di(2-ethylhexyl)adipate, dibutyl phthalate, fluorocarbons, silicate esters, silanes, esters of phosphorus-containing acids, liquid ureas, ferrocene derivatives, hydrogenated mineral oils, chain-type polyphenyls, siloxanes and silicones (polysiloxanes), alkyl-substituted diphenyl ethers typified by a butyl-substituted bis(p-phenoxy phenyl)ether, phenoxy phenylethers.

It is to be understood, however, that the compositions contemplated herein can also contain other materials. For example, corrosion inhibitors, extreme pressure agents, viscosity index improvers, co-antioxidants, antiwear agents and the like can be used. These materials do not detract from the value of the compositions of this invention, rather these materials serve to impart their customary properties to the particular compositions into which they are incorporated.

Mineral oil heat exchange fluids particularly contemplated in accordance with the present invention have the following characteristics: high thermal stability, high initial boiling point, low viscosity, high heat-carrying ability and low corrosion tendency.

In addition, the oxidation and corrosion resistance of functional fluids such as hydraulic fluids and circulating/gear oils can be significantly improved by the adducts of the present invention.

The adducts of the present invention may be employed in any amount which is effective for imparting the desired degree of oxidation improvement, or antiwear improvement or corrosion prevention in accordance with the invention. In many applications the adducts are effectively employed in amounts from 0.01 to 10% by weight, and preferably from about 0.1 to about 1.0% of the total weight of the composition.

DESCRIPTION OF SPECIFIC EMBODIMENTS

The following examples and comparative data will serve to illustrate the novel adducts of the present invention, and the marked improvement in antioxidant, antitrust and antiwear properties of oleaginous materials containing said adducts. It will be understood, however, that it is not intended that the invention be limited to the particular compositions containing those adducts described herein. Various modifications of those adducts and compositions can be employed, as will be readily apparent to those of ordinary skill in the art.

EXAMPLE 1

Adduct of Tolyl Triazole and Aromatic Amine Phosphate

A mixture of 100 grams of tolyl triazole and 300 grams of aromatic amine phosphate salt obtained commercially (Ciba-Geigy Irgalube Registered TM. 349, see also U.S. Pat. No. 4,371,447) was gradually heated to a temperature of 95° C. with stirring. After the mixture had been stirred at that temperature for a period of two hours, the resulting product became quite clear and the reaction was immediately discontinued. The reaction product was cooled to room temperature with continuous stirring. The final product was clear and very viscous at room temperature.

The same method was used with mixtures of tolyl triazole or benzotriazole and other amine phosphate salts. These mixtures yielded similar products. When the weight ratio between tolyl triazole and amine phosphate salts was varied, the viscosity of the final product varied under identical methods of preparation.

Evaluation of the Product

Three different blends or reference oils were used in evaluating the adducts of the present invention. Their respective compositions are disclosed in Table 1 below.

The oxidation stability, antiwear and rust preventive properties of synthetic circulating/gear oils were determined and the data set fourth in Table 2 where the indicated blends of synthetic base oil A were compared: a blend containing (alkyl) dinonyl phenyl phosphonate (Example a); a blend containing the aromatic amine phosphonates (Example b) and a blend (Example c) containing the aromatic amine phosphate—tolyl triazole adduct in accordance with the invention (Example 1). Each of the blends contained equal amounts of the designated additive. The base oil contained no additional additives other than as set forth in Table 1.

Rotary Bomb Oxidation Test (RBOT)—ASTM D-2272

The test oil, water, and copper catalyst coil, contained in a covered glass container, are placed in a bomb equipped with a pressure gage. The bomb is charged with oxygen to a pressure of 90 psi, placed in a constant temperature oil bath set at 150° C., and rotated axially at 100 rpm at an angle of 30 deg from the horizontal. The time for the test oil to react with a given volume of oxygen is measured, completion of the time being indicated by a specific drop in pressure.

Rust Test—ASTM D-665

This method involves stirring a mixture of 300 ml. of the oil under test with 30 ml. of distilled or synthetic sea water, as required, at a temperature of 140° F. (60° C.) with a cylindrical steel specimen completely immersed therein. It is customary to run the test for 24 hours; however, the test period may, at the discretion of the contracting parties, be for a shorter or longer period. Here the test was run for 24 hours using synthetic sea water at 140° F.

Catalytic Oxidation Test

The adducts were blended into the respective base oils. The oils were then subjected to a stream of air at the rate of 5 liters per hour at a temperature of 325° F. for 40 hours in the presence of metals having pro-oxidant properties: iron, copper, lead and aluminum. The lead sample has weighed before and after the test, since lead is one of the metals more susceptible to corrosion by oxidation. The test measurements are: change in acidity or neutralization number as measured by ASTM D-974, change in kinematic viscosity at 210° F., lead loss in milligrams and sludge. Results of the tests are presented in Table 2 and Table 3.

TABLE 1

| COMPOSITION OF REFERENCE OILS | | | |
|---|---|---|---|
| | Synthetic Oil A | Synthetic Oil B | Mineral-Based Oil* C |
| SHF | 79.50 | 80.00 | — |
| Ester | 20.00 | 20.00 | — |
| 150" SPN | — | — | 99.75 |
| Hindered Phenol | 0.50 | — | — |
| DBPC (2, 6 di-t-butyl-p-cresol) | — | — | 0.25 |

*A neutral solvent refined mineral oil having a viscosity at 100° F. of 150 SUS.

TABLE 2
COMPARISON FOR SYNTHETIC CIRCULATING/GEAR OILS

| | Base Oil | Sample a | Sample b | Sample c |
|---|---|---|---|---|
| Synthetic Oil A (SHF) | 100 | 99.80 | 99.80 | 99.80 |
| Alkylphenylphosphonate | | 0.20 | — | — |
| Aromatic Amine Phosphate | | — | 0.20 | — |
| Adduct of Aromatic Amine Phosphate and Tolyl Triazole (Example 1) | | — | — | 0.20 |
| ASTM Rust Test Dist. water, 24 hr @ 60 C. | Fail | Fail | Pass | Pass |
| Rotary Bomb Oxidation Test, Minutes | 250 | 255 | 220 | 480 |
| Catalytic Oxidation Test (325 F., 72 hr) | | | | |
| Visc Incr, % | 59.2 | 68.4 | 94.0 | 16.2 |
| NN Incr | 10.4 | 9.7 | 11.9 | 0.7 |

SHF = Synthetic Hydrocarbon Fluid

TABLE 3
COMPARISON FOR MINERAL-BASED CIRCULATING GEAR OILS

| | Sample d | Sample e | Sample f |
|---|---|---|---|
| Mineral-based Oil | 99.80 | 99.80 | 99.80 |
| Commercial Additive (Oleic Acid plus Long Chain Pentamine) | 0.20 | — | |
| Aromatic Amine Phosphate | | 0.20 | |
| Adduct of Aromatic Amine Phosphate and Tolyl Triazole* (Example 1) | | — | 0.20 |
| Demulsibility, Minutes to 0 ml | 25 | 11 | 9 |
| ASTM Rust Test, Dist Water, 24 hr @ 60 C. | Pass | Pass | Pass |
| Rotary Bomb Oxidation Test, min | 320 | 300 | 640 |
| Mobil Catalytic Oxidation Test (325 F., 72 hr) | | | |
| Visc Incr, % | 51.1 | 19.3 | 12.6 |
| NN Incr, % | 3.8 | 3.0 | 0.7 |
| Visual Sludge | Heavy | Light | Trace |

Solvent refined mineral oil base stock
*In accordance with the invention

The effectiveness of adducts in accordance with the invention were also evaluated as antiwear/extreme pressure additives using the Standard Four-Ball Wear Test and the Timken Load Test. Synthetic Reference Oil B was used for this evaluation. One example, sample g, contained a standard additive package only which consisted of sulfurized isobutylene, silicone defoament, and BASF Wyandotte's Pluronic polyols. The second Example, sample h, contained the standard additive package plus Example 1 in accordance with the present invention. The effectiveness of Example 1 as an antiwear and EP additive is demonstrated by the data set forth in Table 4.

The Standard Four-Ball Wear Test is disclosed in U.S. Pat. No. 3,423,316. In general, in this test three steel balls of 52–100 steel are held in a ball cup. A fourth ball positioned on a rotatable vertical axis is brought into contact with the three balls and is rotated against them. The force with which the fourth ball is held against the three stationary balls may be varied according to a desired load. The test lubricant is added to the ball cup and acts as a lubricant for the rotation. At the end of the test, the steel balls are investigated for wear-scar; the extent of scarring represents the effectiveness of the lubricant as an antiwear agent (Table 2).

The Timken Load Test—ASTM D2782 may be summarized as follows: It determines the load carrying capacity of lubricating fluids by means of the Timken extreme pressure tester. The tester is operated with a steel test cup rotating against a steel test block. The rotating speed is 800±5 rpm. Fluid samples are preheated to 37.8±2.8° C. before starting the test. Timken OK load is the maxiimum load value at which the rotating cup will not rupture the lubricant film and cause scoring or seisure between the rorating cup and the stationary block.

TABLE 4
EP/ANTIWEAR PROPERTIES

| | Sample g | Sample f |
|---|---|---|
| Synthetic Oil B (SHF) | 98.60 | 97.90 |
| Standard Additive Package* | 1.40 | 1.40 |
| Example 1 | — | 0.70 |
| Four-Ball Wear Test, mm 40 kg, 1800 rpm, 200 F., 1 hr | 0.70 | 0.35 |
| Timken OK Load, lb | 50 | 65+ |

Example 1 was also tested in a mineral-based oil. The data is shown in Table 3.
*See page 10 for composition.

It is apparent from the data of Tables 2, 3 and 4 that the adducts of the present invention are markedly effective not only as oxidation stabilizers but also as antiwear and rust preventative additives in both mineral and synthetic oils.

While this invention has been described with reference to preferred compositions and components therefor, it will be understood by those skilled in the art that departure from the preferred embodiments can be effectively made and are within the scope of the present specification.

We claim:

1. A lubricant composition comprising a major amount of an oil of lubricating viscosity or grease prepared therefrom and a minor effective antioxidant, antirust and antiwear improving amount of of a triazole adduct of an amine phosphate obtained by reacting said triazole and said amine phosphate in a 1:3 to about 3:1 ratio of triazole to amine phosphate and carried out at temperatures ranging from about 80° C. to about 125° C. for about 1 to about 8 hours at ambient or higher pressures.

2. A lubricant composition as described in claim 1 wherein the triazole has the following formula

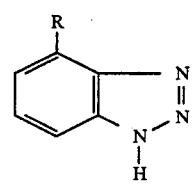

wherein R is H or lower alkyl and the amine phosphate has the generalized formula

wherein x+y=3 and AR=aromatic.

3. The composition defined in claim 1 wherein the triazole is tolyl triazole.

4. The composition as defined in claim 1 wherein the triazole is benzotriazole.

5. The composition as defined in claim 1 wherein the amine phosphate is selected from an aryl or alkaryl aromatic amine phosphates.

6. The composition as defined in claim 2 wherein the triazole is tolyl triazole.

7. The composition of claim 2 wherein the triazole is benzotriazole.

8. The lubricant composition defined in claim 6 wherein the triazole adduct is present in an amount from about 0.001 to about 10 percent by weight.

9. The lubricant composition defined in claim 8 wherein the triazole adduct is present in an amount from about 0.1 to 1.0 percent by weight.

10. The composition of claim 1 wherein the oil of lubricating viscosity is selected from mineral oils or fractions thereof, synthetic oils or mixtures of mineral and synthetic oils.

11. The composition of claim 10 wherein the lubricating oil is adapted for use as a circulating/gear oil.

12. The composition of claim 10 wherein the oil of lubricating viscosity is a mineral oil.

13. The composition of claim 10 wherein the oil of lubricating viscosity is a synthetic oil.

14. The composition of claim 11 wherein the lubricating oil is a mineral oil.

15. The composition of claim 11 wherein the lubricating oil is a synthetic oil.

16. An additive compound having improved antioxidant, antirust and antiwear characteristics prepared by reacting under reaction conditions comprising temperatures ranging from about 80° C. to about 125° C. for about 1 to about 8 hours at ambient or higher pressures, a triazole with an amine phosphate wherein the triazole has the following generalized formula

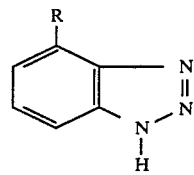

wherein R is H or lower alkyl and the amine phosphate has the generalized formula

wherein $x+y=3$ and $AR=$aromatic.

17. The additive compound of claim 16 wherein the triazole is tolyl triazole.

18. The additive compound of claim 16 wherein the triazole is benzotriazole.

* * * * *